United States Patent [19]

Kitajima et al.

[11] 4,292,272
[45] Sep. 29, 1981

[54] MULTILAYER ANALYSIS SHEET FOR ANALYZING LIQUID SAMPLES

[75] Inventors: Masao Kitajima; Fuminori Arai; Asaji Kondo, all of Asaka, Japan

[73] Assignee: Fuji Photo Film Co., Ltd., Minami-ashigara, Japan

[21] Appl. No.: 157,737

[22] Filed: Jun. 9, 1980

[30] Foreign Application Priority Data

Jun. 8, 1979 [JP] Japan .................................. 54-72047

[51] Int. Cl.³ ..................... G01N 21/84; G01N 33/53; G01N 33/50
[52] U.S. Cl. ......................................... 422/57; 422/56
[58] Field of Search ........................ 422/56, 57, 58, 66

[56] References Cited

U.S. PATENT DOCUMENTS

| | | |
|---|---|---|
| 3,992,158 | 11/1976 | Przbylowicz et al. ............. 422/58 X |
| 4,046,154 | 9/1977 | Johnston et al. ...................... 422/56 |
| 4,050,898 | 9/1977 | Goffe et al. ............................ 422/57 |
| 4,144,306 | 3/1979 | Figueras ................................. 422/56 |

Primary Examiner—Ronald Serwin
Attorney, Agent, or Firm—Sughrue, Mion, Zinn, Macpeak and Seas

[57] ABSTRACT

A multilayer analysis sheet for analyzing liquid samples is described, comprising, in sequence, a light transmitting hydrophobic support having on one side thereof at least one layer containing at least one reagent in a binder and a liquid sample spreading layer made of fabric, which layers are laminated to form an integral unit together with the support, wherein said fabric has the ability to supply a liquid sample placed on the surface thereof to the reagent-containing layer at a substantially constant volume per unit area, which ability is conferred upon the fabric by rendering it hydrophilic; the multilayer analysis sheet can be economically manufactured without variations in quality, and improves the spreading capability of liquid samples.

16 Claims, 4 Drawing Figures

MULTILAYER ANALYSIS SHEET FOR ANALYZING LIQUID SAMPLES

BACKGROUND OF THE INVENTION

1. Field of the Invention

The present invention relates to a multilayer analysis sheet for analyzing liquid samples, and more particularly, it is concerned with a multilayer analysis sheet which enables quantitative determination of a specific chemical component in a liquid sample using a dry-type process which does not require the precise measurement of a definite volume of liquid sample and the weighing of and subsequent preparation of essential reagent(s). As used herein, the terminology "liquid sample" refers to a sample containing water as a solvent.

2. Description of the Prior Art

Multilayer analysis sheets are known which can be used to determine some specific chemical components contained in a liquid sample with ease and that, with high speed in a dry-type process. For instance, the specific examples of such analysis sheets are described in Japanese Patent Application (OPI) Nos. 53888/74 (U.S. Pat. Nos. 3,992,158), 137192/75 (U.S. Pat. No. 3,983,005), 40191/76 (U.S. Pat. No. 4,042,335), 3488/77 (U.S. Pat. No. 4,006,403), 131786/77 (U.S. Pat. No. 4,050,898), 131089/78 (U.S. Pat. No. 4,144,306), 29700/79 (U.S. Pat. No. 4,166,093) and 34298/79 (British Patent Application GB No. 2,000,869A) (the term "OPI" as used herein refers to a "published unexamined Japanese patent application"), U.S. Pat. Nos. 4,110,079 and 4,132,528, *Clinical Chemistry*, Vol. 24, pp. 1335–1350 (1978), and so on. Such multilayer analysis sheets have a common format, wherein a spreading layer capable of spreading liquid samples, layers containing reagents essential to the analysis, and so on are laminated in advance on a support, and, upon the actual chemical analyses using these sheets, quantitative analysis can be conducted through only two basic procedures. One procedure involves allowing a drop of the sample liquid to be examined to adhere onto the sheet, and the other is to evaluate the extent of change in color using a densitometer. Therefore, these procedures are referred to as dry chemical analyses, as they do not require procedures which are indispensable for conventional methods, such as: arrangement of test tubes; preparation, volume-measurement, and addition of reagent solutions; accurate weighing-out of samples; and so on.

The basic structure of the multilayer chemical analysis sheet of the type described above is constructed of a support, a reagent layer and a sample spreading layer, which are arranged in this order. The reagent layer is obtained by spreading reagent(s) incorporated in a binder like gelatin in a form of thin layer, which may have a monolayer structure or a multilayer one. The multilayer structure is constructed of a first reagent layer, the second reagent layer and so on, wherein reagents are contained separately, being classified in the order of reaction, and optionally, it can involve a detecting layer, a dye-receiving layer, and the like. In addition, interlayers such as a radiation-blocking layer, a barrier layer and the like can be provided between the spreading layer and the reagent layer, or between each pair of layers containing different reagents respectively. The sample spreading layer is arranged at the outermost position of an analysis sheet, and corresponds to the face to which liquid samples are to be adhered. The function of this layer is to supply a liquid sample to the reagent layer at an approximately constant volume per unit area regardless of its applied volume, that is to say, this layer acts as a spreader for a liquid sample. The action of spreader layer, then, is simply to allow a liquid sample placed on the sample spreading layer in a measured volume of x $\mu$l, 2x $\mu$l, 3x $\mu$l ... to spread on the sample spreading layer in proportion to the volume of the sample put thereon through the spreading action inherent in the layer; namely, to spread so as to cover an area of y $cm^2$, 2y $cm^2$, 3y $cm^2$..., respectively and consequently, to render the quantity of the sample to be supplied to the reagent layer per unit area approximately constant. This means that a liquid sample can be analyzed quantitatively without precise measurement of the volume thereof upon analysis, and this has an important significance.

The mechanism of spreading is not fully understood, but it is theorized that spreading results from and is limited by a combination of forces such as hydrostatic pressure of a liquid sample, capillary action within the spreading layer, surface tension of the sample, wicking action of layers in fluid contact with the spreading layer, and the like. As will be appreciated, the extent of spreading is dependent in part on the volume of liquid to be spread. However, it should be emphasized that the uniform concentration obtained with spreading is substantially independent of liquid sample volume and will occur with varying degrees of spreading. As a result, elements of this invention do not require precise sample application techniques. However, a particular liquid sample volume may be desirable for reasons of preferred spread times or the like. Because the elements of this invention are able to produce quantitative results using very small sample volumes that can be entirely taken up within a conveniently sized region of the spreading layer (e.g., one square centimeter), there is no need to remove excess moisture from the element after application of a liquid sample. Further, because spreading occurs in the spreading layer and the spread substance is provided to the fluid contacting reagent layer and without apparent substantial lateral hydrostatic pressure, there is not the "ringing" problem often seen with prior analytical elements when soluble reagents were used.

The spreading layer need only produce a uniform concentration of spread substance per unit area at its surface facing a layer with which the spreading layer is in contact.

Liquid sample spreading layers having such a sample spreading action as described above are described in detail in the aforementioned patent specifications and literature, which state that non-fibrous porous media alone are effective for the use as the layer possessing the above-described spreading action.

Examples of such non-fibrous porous medium include brush polymers (that is, membrane filters), diatomaceous earth, dispersions obtained by dispersing porous substances like microcrystalline materials (e.g., microcrystalline cellulose (Avicel, trademark of FMC Corporation)) in binders, porous aggregates formed by allowing fine spherical beads of glass or resin to adhere to one another in point-to-point contact, and so on. It is necessary for these non-fibrous porous media to have an isotropic porous form, that is to say, a form in which voids are distributed uniformly in all directions of the medium, as stated in U.S. Pat. No. 3,992,158.

There are two methods employable for the formation of the spreading layer consisting of such non-fibrous isotropically porous medium having the described liquid sample-spreading action. The first method involves lamination of an isotropically porous sheet, such as a commercially available membrane filter, on the reagent layer or a radiation-blocking layer, and subsequent adhesion of the sheet thereto. The nature of the radiation-blocking layer is well described in U.S. Pat. No. 4,042,335. This method is disadvantageous from technical and economic points of view, since the membrane filter is fragile and expensive. The second method involves coating a material capable of forming an isotropic porous medium layer; for example, material containing as a main component a solution of cellulose acetate in an acetone-dichloroethane (1:1) solution mixture; the same material containing additionally diatomaceous earth; a material prepared by dispersing glass beads of 80 to 120 mesh in a small amount of gelatin, and so on. The material is coated on the reagent layer, and upon subsequent drying of the layer coated under appropriate conditions the layer coated can be transformed into a homogeneous porous layer. No specific means is required for the drying. Usually, the drying is carried out by blowing air or an inert gas such as nitrogen gas, or by spontaneous drying, at temperatures of about 15° to 80° C., preferably 20° to 50° C. Many technical difficulties arise in the actual preparation according to the second method. For example, in manufacturing the porous spreading layer, it is technically difficult to control the voids contained in each product so as to obtain a uniform material and that, settled size, arrangement, volume ratio and so on. Moreover, in some cases it happens that reagents contained in the reagent layers are extracted with solvents used in the coating materials to cause diffusion of the reagents into the spreading layers. Further, when liquid samples containing proteins in high concentration, such as sera, are to be examined, what is more important is the defect that the sample-spreading action turns out to be essentially non-quantitative in the sample spreading layers made up of known non-fibrous porous media, because the spreading varys appreciably depending upon the protein content in the liquid sample on the layer. Furthermore, when whole blood samples are being tested, the sample spreading layers of the types described above suffer from the defect that the sample-spreading action therein turns out to be even less quantitative because it varys to a great extent depending upon the content of a solid component in addition to that of proteins.

SUMMARY OF THE INVENTION

Liquid sample-analyzing multilayer analysis sheets provided according to this invention have the same use as the known sheets described above. As for the sample-spreading layer, known ones, however, suffer from the above-described defects. Thus, as a result of a search for a solution of such defects as are described above, fabrics which have received a treatment so as to render them hydrophilic have now been found to be usable as layers capable of spreading liquid samples without attended by such disadvantages as described above and thereon the present invention is based. By using a hydrophilic type fabric as the spreading layer, various defects from which known non-fibrous porous media suffer can be completely eliminated, such that the production of the spreading layer is facilitated, the quality of the spreading layer does not vary, the sample-spreading property is improved, and so on.

Thus a multilayer analysis sheet for analyzing liquid samples according to this invention comprises, in sequence, a light transmitting hydrophobic support having on one side thereof at least one layer containing at least one reagent in a binder, and a liquid sample spreading layer made of fabric, said layers being laminated to form an integral unit together with the support, and wherein the liquid sample spreading layer is made of fabric having an ability to supply a liquid sample placed on the surface thereof to the reagent-containing layer at a substantially constant volume per unit area, wherein said ability is conferred by treatment to render the fabric hydrophilic.

DETAILED DESCRIPTION OF THE INVENTION

Figure 4:
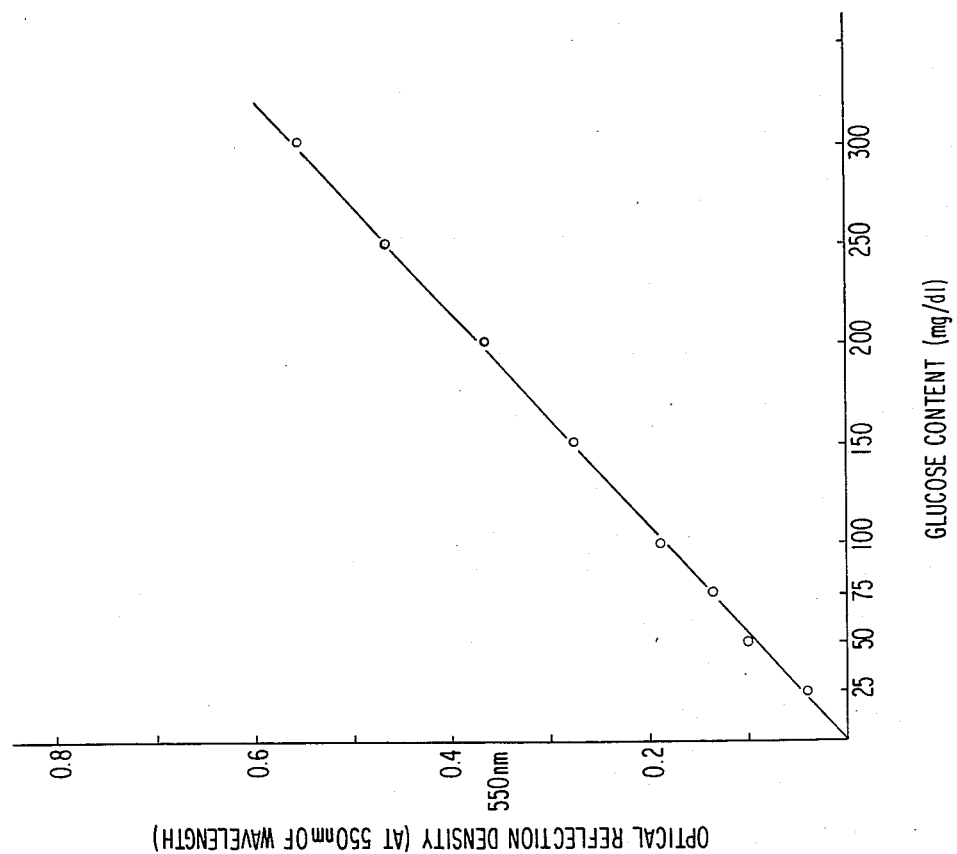
FIG. 4 is a graph showing a correlation of the glucose content in pseudo serum to the optical reflection density measured using the multilayer analysis sheet prepared in Example 1 of the present invention, for the purpose of analyzing liquid samples.

An important feature of multilayer analysis sheets provided according to this invention is, as already described, that hydrophilic type fabrics are employed as the liquid sample-spreading layer. Hydrophilic type fabrics refers to fabrics whose "wetting" with respect to water is improved by treating them with surface active agents, wetting agents, hydrophilic polymers and the like. As an indication of "wetting" properties, it is feasible to adopt the time taken from the moment when a 10 $\mu l$ of 7% aqueous solution of cattle albumin is placed on the fabric until the moment when the spreading of the aqueous solution on the fabric comes to an end, taking advantage of the phenomenon that an aqueous solution placed on fabric spreads describing concentric circles in all directions on the face of the fabric as the solution is absorbed in the direction of the thickness of the fabric, and, after some period of time, the spreading of the aqueous solution comes to an end and the movement thereof becomes stationary. In the present invention, fabrics having the characteristic that it takes preferably 30 seconds or less, more preferably 15 seconds or less, and more preferably 10 seconds or less, to conclude the spreading of a 7% cattle albumin aqueous solution on the fabrics can be employed. In order to test for such a characteristic, a test plate is first prepared by providing a gelatin layer having a dry thickness of 10 $\mu m$ on a transparent glass plate, wetting the gelatin layer lightly with water, and then, by laminating the gelatin layer on the hydrophilic property-conferred fabric, followed by drying. Then, a 10 μl sample of 7% cattle albumin aqueous solution colored by a certain dye is placed on the fabric. The time taken to conclude the spreading of the colored solution on the fabric is measured. Furthermore, after few minutes the gelatin layer is examined for uniformity of coloration by the observation from the side of the glass plate. The spreading time of the colored cattle albumin aqueous solution and the uniformity of coloration in the gelatin layer vary depending upon the kind of fabric on which the solution is placed, the kind of the treatment used for rendering the fabric hydrophilic, and the manner for carrying out such a treatment. The term substantially uniform means that variance allowed for a volume of the liquid sample supplied to the reagent layer per the unit area thereof through the spreading action of fabric is within the range of about 10% or less in every part of the reagent layer.

A wide variety of fabrics can be employed as the liquid sample spreading layer, and of various fabric tissues, plain weave, which is formed by weaving warp and weft yarns alternately, is preferably used. As for warp and weft which compose plain weave, a desirable count ranges from 20 to 120. Of fabrics having the tissue called plain weave, cotton fabrics of types named close cloth, canequim, broadcloth and poplin are preferably employed. In addition to other natural fibers woven in the same manners as in the above-described cotton fabrics (e.g., kapok, flax, hemp, ramie, silk and so on), fabrics obtained by weaving mixed yarns of chemical fiber (e.g., viscose rayon, cupro-ammonium rayon, cellulose acetate, vinylon, polyethylene terephthalate or so on) and cotton fiber in the same manners as in the above-described cotton fabrics, and fabrics obtained by weaving chemical fiber yarn in the same manners as in the above-described cotton fabrics can be also employed.

As examples of processes for rendering fabrics hydrophilic, mention may be made of a process in which commercially produced fabrics are washed and rinsed thoroughly with water to remove starch and other processing materials therefrom and optionally they are further dipped with from 1 to 5% aqueous solutions of surface active agents; a process in which surface active agents are made to incorporate into fabrics in proportion of 0.1 to 10% per unit weight of fabric by spraying aqueous solutions of surface active agents onto the fabrics to wet them and then by drying them; and so on. Therein, any types of water-soluble surface active agents, namely, nonionic, cationic, anionic and amphoteric agents, can be used. However, nonionic surface active agents such as alkylaryl ethers of polyoxyethylene and polyglycerine, fatty acid esters thereof, sorbitol esters thereof and the like are particularly preferable to other types of surface active agents from the standpoint that the nonionic ones cause hemolysis to much less extents.

In another type of the process for rendering fabrics hydrophilic, fabrics are wet with hydrophilic polymer solutions, which may contain fine powders such as titanium oxide, barium sulfate and the like, and wetting agents such as glycerine, polyethylene glycol and the like, in addition to hydrophilic polymers such as gelatin, polyvinyl alcohol and the like, and then dried. Hydrophilic polymers are incorporated in fabrics in proportion of from about 0.05 to 10% by weight and preferably from about 0.1 to 5% by weight, per unit weight of fabric.

When the processing agents employed for rendering fabrics hydrophilic, that is to say, surface active agents and hydrophilic polymers, are incorporated in fabrics in excessive amounts, the texture of fabric and surface of yarn composing fabric are covered with the processing agents. In other words, they receive a so-called starching treatment, and they can cause deterioration of the liquid sample-spreading action. Therefore, the addition amounts of processing agents should be adjusted experimentally with respect to each fabric used to such an extent that an apparent change in the surface condition of yarn composing fabric may not be yet caused by the addition of processing agents.

It is thought that excellent, liquid sample-spreading action which fabric acquires through such a treatment as to render hydrophilic results from the compounded anisotropic porosity of fabric, which is constituted by microscopical anisotropic porosity which both warp and weft composing fabric have predominantly along the direction of the length of yarn and macroscopical anisotropic porosity which originates from texture formed by warp and weft, and lies along the direction perpendicular to the plane of fabric and that, which porosities cooperate with each other to exhibit synergistic effect.

Figure 1:
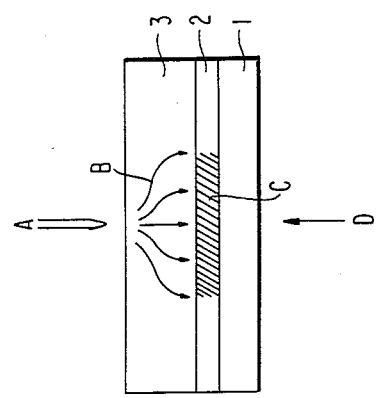
FIGS. 1 to 3 are schematic cross-section diagrams of the multilayer analysis sheets for analyzing liquid samples, which each is produced in accordance with an embodiment of this invention. Therein, Arabic numerals and capital letters have the respective meanings stated below: 1 indicates a light transmitting hydrophobic support, 2 indicates a reagent layer, 3 indicates a liquid sample spreading layer made of a fabric according to the invention, 4 indicates an analytic function supporting layer, 5 indicates a structural auxiliary layer, A indicates the location on which a liquid sample is placed, B indicates directions along which a liquid sample is spread uniformly, C indicates a color-spread or a color changed region, and D indicates the direction from which observations are carried out.

Next, a basic structure of the liquid sample analyzing multilayer analysis sheet of the present invention is illustrated using the schematic cross-section diagram of FIG. 1. The multilayer analysis sheet has such a structure that a reagent layer 2 is provided on a light transmitting hydrophobic support 1 and a liquid sample spreading layer 3 made of fabric is provided on the reagent layer to form an integral unit.

Upon putting a drop of a liquid sample on the liquid sample spreading layer in the direction A, the liquid sample is spread uniformly in such directions as to be indicated at arrow B and supplied to the reagent layer by nearly the same fraction of volume per unit area. Consequently, a certain reaction takes place in the reagent layer to result in uniform color formation or color change in the shaded area indicated at C. A quantitative difference in color before and after such a reaction is observed in the direction A and thereby the concentration of a specific component in a liquid sample can be determined colorimetrically.

As the light transmitting hydrophobic support 1 in FIG. 1, known water-impermeable transparent supports of about 50 μm to about 2 mm in thickness, such as films of polyethylene terephthalate, cellulose esters (e.g., cellulose diacetate, cellulose triacetate, cellulose acetate propionate, etc.), polycarbonates, polymethylmethacrylate and like polymers, glass plate and so on, can be employed. The reagent layer 2 is provided by spreading a composition, which is prepared by dispersing and incorporating a reagent for determining a specific component in a liquid sample to be examined in a known hydrophilic binder such as gelatin, polyvinyl alcohol, polyvinyl pyrrolidone, agarose, sodium polyvinyl benzenesulfonate or the like, in a layer 1 μm to 100 μm in thickness. For example, a reagent layer employed for the determination of glucose content in a liquid sample is formed by spreading a composition containing as main components glucose oxidase, peroxidase, aminoantipyrine and 1,7-dihydroxynaphthalene, these four component being dispersed using gelatin, in a layer having a thickness of 10 μm to 20 μm. On this reagent layer, a liquid sample spreading layer 3 made of the fabric which is rendered hydrophilic in advance is laminated and then sticked.

Figure 2:
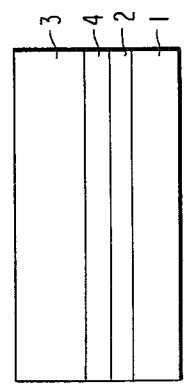
Figure 3:
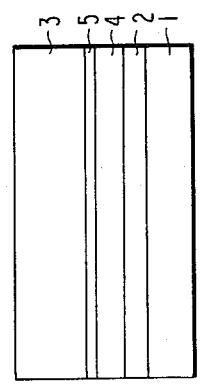

In accordance with a basic embodiment of the present invention, the multilayer analysis sheet for analyzing liquid samples has, as shown in FIG. 1, the liquid sample spreading layer 3 made of the fabric which is positioned adjacent directly to the reagent layer 2 arranged on one side of the support 1. According to another embodiment of the present invention, an analytical function supporting layer 4, for example, a radiation-blocking layer or a light reflecting layer, is provided on the reagent layer. Then, the liquid sample spreading layer 3 made of the fabric is laminated on the layer 4, as shown in FIG. 2. According to a still another embodiment of the present invention, a structural auxiliary layer 5 such as an adhesive layer is further provided on the analytical function supporting layer 4 such as a radiation-blocking layer or a light reflecting layer, which is provided on the reagent layer 2, and then the liquid sample spreading layer made of the fabric is laminated on the layer 5, as shown in FIG. 3. In accordance with a further embodiment of the present invention, the structural auxiliary layer 5 such as an adhesive layer is provided directly on the reagent layer and thereon the liquid sample spreading layer made of the fabric is laminated, which is not illustrated in any figures. In every embodiment, the order of arrangement is the same with respect to the support, the reagent layer and the liquid sample spreading layer. The radiation-blocking layer 4 is useful in the case where a liquid sample contains colored particles, as in the case of total blood containing erythrocytes. Since the color of colored particles present on one side of the radiation-blocking layer is screened by this layer, it cannot be perceived at all from the other side of the radiation-blocking layer, that is to say, from the side of the light transmitting support. Therefore, the colored particles do not interfere in colorimetric determinations. The radiation-blocking layer can be prepared by coating a dispersion of a finely divided substance, such as titanium dioxide fine powder, barium sulfate fine powder, aluminium fine powder, tec., in a water-permeable hydrophilic polymer binder in a layer having a thickness of from 5 μm to 100 μm, and preferably is from 5 μm to 30 μm, and permits the passage of liquid components therethrough.

The liquid sample spreading layer of the present invention can also contain one of or all of reagents essential to the analysis. On the occasion that all of the reagents essential to the analysis are contained in the liquid sample spreading layer, the layer corresponding to the reagent layer contains a hydrophilic binder alone. Under such a circumstance also, color formation or color change resulting from the placement of a liquid sample can be observed in this layer. Accordingly, this layer can also be considered in the category of the reagent layer.

The adhesive layer provided as a structural auxiliary layer functions principally to strengthen adhesion force between the reagent layer, or the analytical function supporting layer such as the radiation-blocking layer or the light reflecting layer, and the liquid sample spreading layer made of the fabric. The adhesive layer can be made of hydrophilic polymer used as a binder in the reagent layer or the analytical function supporting layer such as the radiation-blocking layer or the light reflecting layer. In this case, the liquid sample spreading layer made of the fabric is adhered to the adhesive layer by application of proper magnitude of pressure before the hydrophilic polymer of the adhesive layer is dried, or after the hydrophilic polymer is wet with water or an aqueous solution of a surface active agent. The thickness of the adhesive layer can range from about 0.5 μm to 15 μm, and preferably is from 0.5 μm to 5 μm.

The multilayer analysis sheets prepared in accordance with embodiments of the present invention are favorable for determining specific components in liquid samples. For instance, they are especially well suited for quantitative analyses of glucose, urea, bilirubin, cholesterol, protein, enzyme and like components contained in body liquids such as urine, blood and so on. One remarkable feature of the multilayer analysis sheets of the invention is that specific components in blood samples, in serum samples or total blood ones, can be determined without being so much affected by the contents of their components.

EXAMPLE 1

On a colorless transparent polyethylene terephthalate film having a subbing layer suitable for gelatin, a reagent layer for determining glucose was coated, which was constituted with the following proportion of ingredients, in a dry thickness of about 15 μm.

| Composition of Reagent Layer | parts by weight |
| --- | --- |
| Glucose Oxidase | 2 |
| Peroxidase | 1 |
| 1,7-Dihydroxynaphthalene | 5 |
| 4-Aminoantipyrine | 5 |
| Alkali Processed Gelatin | 200 |
| Nonion HS 210 (trademark of polyoxyethylene alkylphenyl ether, products of Nippon Oils & Fats Co., Ltd.) | 2 |

On the reagent layer a water dispersion in which dried gelatin and titanium dioxide fine powder were mixed in a ratio of 1:8 (by weight) was coated at a dry thickness of about 15 μm to form a radiation-blocking layer. In addition, on the radiation-blocking layer an adhesive layer constituted of gelatin containing 0.2% of nonionic surface active agent (Nonion HS 210) was provided, so as to have a dry thickness of about 5 μm. On the other hand, broadcloth woven from cotton yarn of 60 count (products of Nisshin Spinning Co., Ltd.) was processed in a 1% gelatin aqueous solution to provide fabric to be employed as a liquid sample spreading layer, which fabric had a gelatin content of about 2.5%, and thereby became hydrophilic.

The previously prepared analysis sheet for glucose was wet with a 0.2% aqueous solution of nonionic surface active agent (Nonion HS 210) to a nearly uniform extent and thereon, the fabric processed was superposed at once. In order to force them to come into close contact with each other, they were passed through a narrow space between a pair of pressed rollers to form a uniform laminate. The thus-obtained laminate did not delaminate even when it was dried completely. Under such a circumstance, the fabric is said to be firmly adhered to the reagent layer. Thus, a multilayer analysis sheet for determining glucose was obtained.

On the thus-obtained multilayer analysis sheet for determining glucose, a 10 μl portion of pseudo serum containing 7% of cattle albumin and 100 mg/dl of glucose was placed. It took about 2 seconds to complete the spreading of the pseudo serum. Then, the resulting analysis sheet was incubated for 10 minutes in a thermostat maintained at 37° C. The pseudo serum was spread in a shape of disk measuring about 10 mm in diameter, and produced circular, spread color image having appropriately uniform color density, which exhibited its absorption maxima at the wavelength of 495 nm, in the reagent layer of the analysis sheet. The optical reflection density at the center of the spread color image was measured with a Macbeth reflection densitometer RD 504 (maximum transmission wavelength: 550 nm). The optical density obtained was 0.19.

Further, nine pseudo serum samples, in which glucose was contained in concentrations of 25, 50, 75, 100, 150, 200, 250 and 300 mg/dl, respectively, were prepared. Each of these samples was put on a multilayer analysis sheet of the kind described above, and the spread color density was measured in the same manner as described above. The results of these measurements prove that the concentration of glucose in pseudo serum and the optical reflection density of the spread color image bear a linear relationship to each other, as shown in FIG. 4.

FIG. 4 shows that the concentration of glucose in serum can be determined in the process including the steps of putting serum on the analysis sheet for the determination of glucose prepared in the present invention and measuring the optical reflection density of the resulting sheet.

EXAMPLE 2

A multilayer analysis sheet for the determination of glucose was prepared in the same manner as in Example 1 except that as the fabric for the liquid sample spreading layer, broadcloth obtained by weaving mixed yarn of 60 count cotton yarn and polyester (PET) fiber (cotton fraction: 35%, polyester fraction: 65%) (the products of Kuraray Co., Ltd.), which was impregnated with water, into which 0.5 wt% of gelatin and 5 wt% of titanium dioxide fine powder were dispersed, under such a condition as to adjust the content of the impregnant to 3.2 wt% in a dry state to be rendered hydrophilic, was employed.

In a similar manner as in Example 1, a 10 $\mu$l portion of pseudo serum sample containing 100 mg/dl of glucose was put on the liquid sample spreading layer, followed by incubation and then the optical reflection density of the spread color image was measured. The optical density obtained was 0.19. Further, in analogy with Example 1, optical reflection density measurements on a series of pseudo serum samples differing in glucose content yielded a straight line when plotted against the glucose content and therefrom it can be seen that the glucose content can be determined with high accuracy.

EXAMPLE 3

A multilayer analysis sheet for the determination of glucose was prepared in the same manner as in Example 1 except that 100% cotton calico (in which 60 count yarn was used), which was previously treated with a 0.5% aqueous solution of Triton X-100 (trade name of nonionic surface active agent produced by Rohm & Haas Co.; isooctylphenylpolyethoxy alcohol) instead of gelatin in Example 1, was employed as the fabric for the liquid sample spreading layer.

A 10 $\mu$l portion of fresh blood (containing heparin) drawn from a healthy person was put on the liquid sample spreading layer made of the fabric of the above-described analysis sheet. The blood sample was spread rapidly and uniformly by analogy with the analysis sheet of Example 1. Thereafter, it took about 12 seconds to complete the spreading and the diameter of the circle spread was about 9 mm.

After the resulting analysis sheet was incubated for 10 minutes at 37° C. in the same manner as in Example 1, the optical reflection density thereof was measured. The optical density measured was 0.16.

EXAMPLE 4

An experiment was carried out in the same manner as in Example 1, except that a multilayer analysis sheet for the determination of glucose was prepared as follows: Instead of providing the adhesive layer comprising gelatin containing a 0.2% nonionic surface active agent (Nonion HS 210) on the radiation-blocking layer, the radiation-blocking layer was wet with a 0.2% aqueous solution of nonionic surface active agent (Nonion HS 210) to a nearly uniform extent and immediately, passed through narrow space between pressed rollers as they were allowed to come into a face-to-face contact with the fabric to be employed as the liquid sample spreading layer. Similar results to those in Example 1 were thus obtained.

Therein, the bonding strength between the reagent layer and the liquid sample spreading layer made of the fabric in the multilayer analysis sheet prepared in this Example was ½ time that between such layers in the multilayer analysis sheet prepared in Example 1. However, the liquid sample spreading layer was not delaminated from the reagent layer throughout analytical procedures in this Example also. Therefore, this sheet can also be said to be well-suited for practical use.

While the invention has been described in detail and with reference to specific embodiments thereof, it will be apparent to one skilled in the art that various changes and modifications can be made therein without departing from the spirit and scope thereof.

What is claimed is:

1. A multilayer analysis sheet for analyzing liquid samples comprising, in sequence, a light transmitting water-impermeable support having on one side thereof at least one layer containing at least one reagent in a binder, and a liquid sample spreading layer made of fabric, said layers being laminated to form an intergral unit together with the support, and wherein said fabric has the ability to supply a liquid sample placed on the surface thereof to said reagent-containing layer at a substantially constant volume per unit area, which ability is conferred upon said fabric by rendering it hydrophilic.

2. A multilayer analysis sheet as in claim 1, wherein said fabric has the characteristic that the spreading of a 7% cattle albumin aqueous solution on the fabric is 30 seconds or less.

3. A multilayer analysis sheet as in claim 2, wherein said fabric has the characteristic that the spreading of the 7% cattle albumin aqueous solution is 15 seconds or less.

4. A multilayer analysis sheet as in claim 2, wherein said fabric has the characteristic that the spreading of 7% cattle albumin aqueous solution is 10 seconds or less.

5. A multilayer analysis sheet as in claim 1, wherein said fabric is rendered hydrophilic by the steps of washing with water and contacting with an aqueous solution containing from 1 to 5% surface active agent.

6. A multilayer analysis sheet as in claim 1, wherein said fabric contains from about 0.05 to 10% by weight of a hydrophilic polymer.

7. A multilayer analysis sheet as in claim 6, wherein the fabric contains from about 0.1 to 5% by weight of the hydrophilic polymer.

8. A multilayer analysis sheet as in claim 1, 2, 3, or 4, wherein said sheet comprises an analytical function supporting layer containing a water-permeable hydrophilic polymer binder between said sample spreading layer and said layer containing at least one reagent in a binder.

9. A multilayer analysis sheet as in claim 8, wherein said analytical function supporting layer is a radiation-blocking layer or a light reflecting layer.

10. A multilayer analysis sheet as in claim 9, wherein said sheet includes a structural auxiliary layer containing a water-permeable hydrophilic polymer binder between said sample spreading layer and said analytical function supporting layer.

11. A multilayer analysis sheet as in claim 10, wherein said structural auxiliary layer is an adhesive layer.

12. A multilayer analysis sheet as claimed in claim 1, wherein said binder is a water-permeable hydrophilic polymer binder, and further wherein said liquid sample is a liquid sample containing water as a solvent.

13. A multilayer analysis sheet as claimed in claim 1, wherein said fabric is formed by weaving warp and weft yarns in a plain weave, wherein the count of said weave ranges between 20 and 120.

14. A multilayer analysis sheet as claimed in any of claims 1 or 12, wherein said fabric is selected from the group consisting of canequim, broadcloth, kapok, flax, hemp, ramie, silk, viscose rayon, cupro-ammonium rayon, cellulose acetate, vinylon and polyethylene terephthalate.

15. A multilayer analysis sheet as claimed in any of claims 1, 2, 3 or 4, wherein said sheet is further comprised of an analytical function supporting layer containing a water-permeable hydrophilic polymer binder between said sample spreading layer and said layer containing at least one reagent in a binder, and wherein said analytical function supporting layer is a radiation-blocking layer or a light-reflecting layer; said sheet further comprising a structural auxiliary layer containing a water-permeable hydrophilic polymer binder between said sample spreading layer and said analytical function supporting layer.

16. A multilayer analysis sheet as claimed in any of claims 1, 2, 3 or 4, wherein said structural auxiliary layer is an adhesive layer.

* * * * *